(12) United States Patent
Sullivan et al.

(10) Patent No.: US 9,451,951 B2
(45) Date of Patent: Sep. 27, 2016

(54) SUTURE SNARE WITH RETRACTABLE SLEEVE

(71) Applicant: Arthrex, Inc., Naples, FL (US)

(72) Inventors: Derek C. Sullivan, Naples, FL (US); Benjamin Wai-Man Chan, Naples, FL (US); Amr W. ElMaraghy, Mississauga (CA)

(73) Assignee: Arthrex, Inc., Naples, FL (US)

( * ) Notice: Subject to any disclaimer, the term of this patent is extended or adjusted under 35 U.S.C. 154(b) by 231 days.

(21) Appl. No.: 14/072,966

(22) Filed: Nov. 6, 2013

(65) Prior Publication Data
US 2014/0128889 A1 May 8, 2014

Related U.S. Application Data

(60) Provisional application No. 61/723,493, filed on Nov. 7, 2012.

(51) Int. Cl.
| | | |
|---|---|---|
| *A61B 17/04* | (2006.01) | |
| *A61B 17/00* | (2006.01) | |
| *A61B 17/29* | (2006.01) | |
| *A61B 17/06* | (2006.01) | |

(52) U.S. Cl.
CPC ....... *A61B 17/0483* (2013.01); *A61B 17/0485* (2013.01); *A61B 17/06109* (2013.01); *A61B 2017/00309* (2013.01); *A61B 2017/00336* (2013.01); *A61B 2017/00349* (2013.01); *A61B 2017/2923* (2013.01)

(58) Field of Classification Search
CPC ..................... A61B 17/04; A61B 2017/06052; A61B 17/0483; A61B 17/00; A61B 17/06; A61B 17/29; A61B 17/06109; A61B 2017/00309; A61B 2017/00336; A61B 2017/00349; A61B 2017/2923; A61F 2002/4623; A61F 2002/9517; A61M 25/0136; A61M 25/0631; Y10S 254/06
USPC ................................ 606/139, 144–148, 232
See application file for complete search history.

(56) References Cited

U.S. PATENT DOCUMENTS

| | | | |
|---|---|---|---|
| 5,250,054 A | 10/1993 | Li | |
| 5,312,422 A | 5/1994 | Trott | |
| 5,364,410 A | 11/1994 | Failla et al. | |
| 5,474,565 A | 12/1995 | Trott | |

(Continued)

FOREIGN PATENT DOCUMENTS

| | | |
|---|---|---|
| EP | 2 236 094 A2 | 10/2010 |
| WO | WO 95/02998 A1 | 2/1995 |

(Continued)

*Primary Examiner* — Jonathan Miles
*Assistant Examiner* — George J Ulsh
(74) *Attorney, Agent, or Firm* — Blank Rome LLP

(57) ABSTRACT

A delivery device (suture passer or suture snare) that may be used in both open and endoscopic surgical procedures. The delivery device is designed with an internal member terminating in a snare and a retractable outer sheath (sleeve). The device is passed through tissue, and the outer sheath is retracted (moved back), allowing the snare to open. The suture is captured by the snare, and the outer sheath is then released so that it returns to its distal position, closing the snare and securing the captured suture. Since the snare is exposed by retracting the outer sheath (sleeve), rather than advancing the snare, the space requirement for the device is reduced, as is the possibility that the snare will undesirably contact sensitive tissue.

18 Claims, 16 Drawing Sheets

(56) References Cited

U.S. PATENT DOCUMENTS

| | | |
|---|---|---|
| 5,499,991 A | 3/1996 | Garman et al. |
| 5,643,292 A | 7/1997 | Hart |
| 5,643,294 A | 7/1997 | Tovey et al. |
| 5,653,716 A | 8/1997 | Malo et al. |
| 5,766,196 A | 6/1998 | Griffiths |
| 5,817,111 A | 10/1998 | Riza |
| 5,836,960 A | 11/1998 | Kolesa et al. |
| 5,910,148 A | 6/1999 | Reimels et al. |
| 5,928,264 A | 7/1999 | Sugarbaker et al. |
| 6,022,360 A | 2/2000 | Reimels et al. |
| 6,102,920 A | 8/2000 | Sullivan et al. |
| 6,629,984 B1 | 10/2003 | Chan |
| 7,291,104 B2 | 11/2007 | Neisz et al. |
| 7,481,824 B2 | 1/2009 | Boudreaux et al. |
| 7,753,904 B2 | 7/2010 | Shelton, IV et al. |
| 8,142,473 B2 | 3/2012 | Cunningham |
| 2004/0147941 A1 | 7/2004 | Takemoto et al. |
| 2009/0157060 A1* | 6/2009 | Teague ............... A61B 17/221 606/1 |
| 2010/0217069 A1* | 8/2010 | Meade ............... A61B 17/0485 600/37 |
| 2010/0228147 A1 | 9/2010 | Suda |
| 2010/0305552 A1 | 12/2010 | Shelton, IV et al. |

FOREIGN PATENT DOCUMENTS

| | | |
|---|---|---|
| WO | WO 2006/023975 A2 | 3/2006 |
| WO | WO 2007/019374 A2 | 2/2007 |

\* cited by examiner

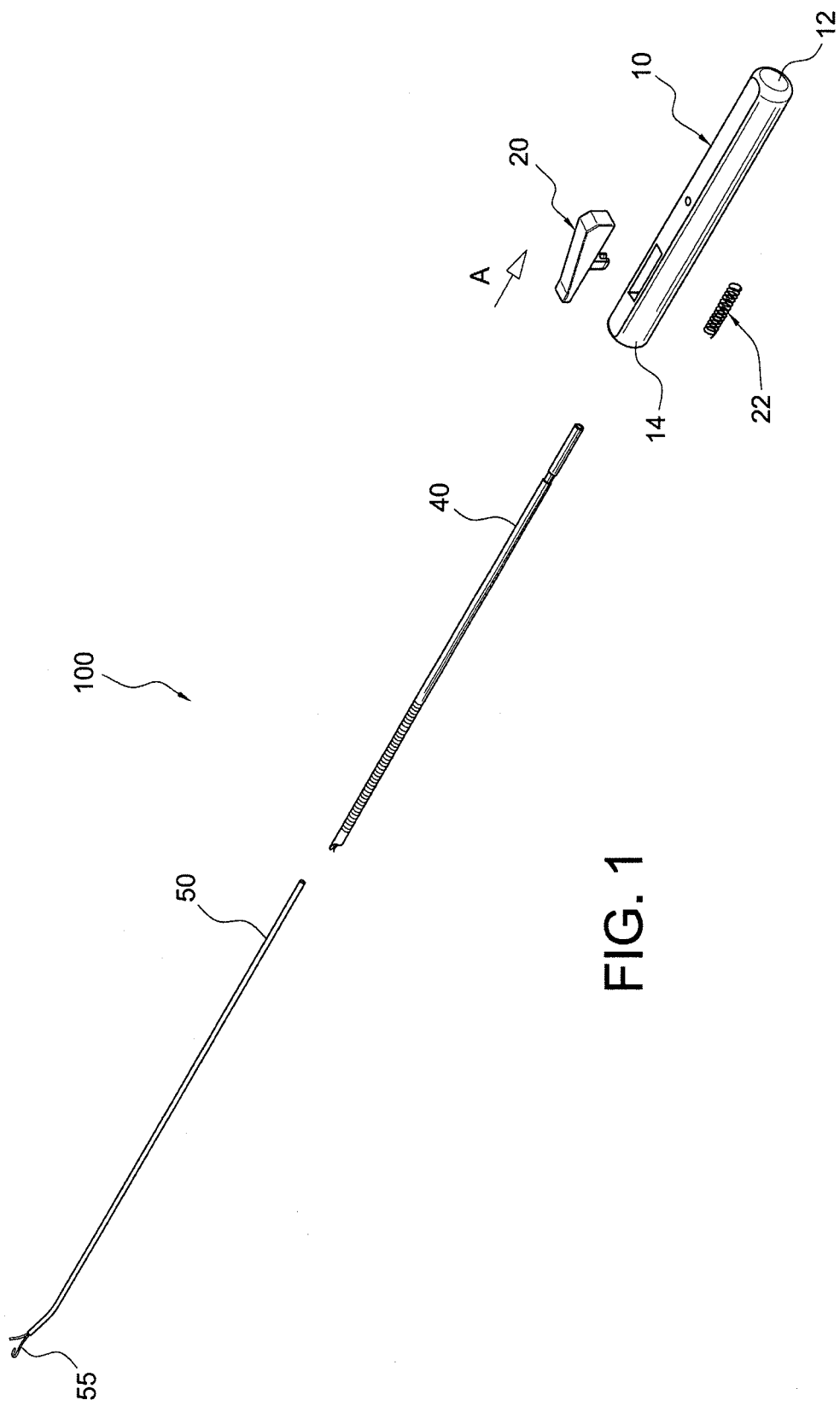

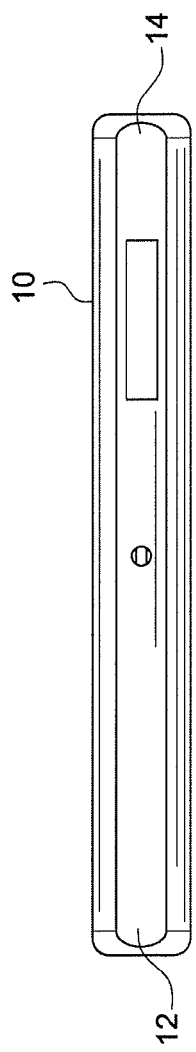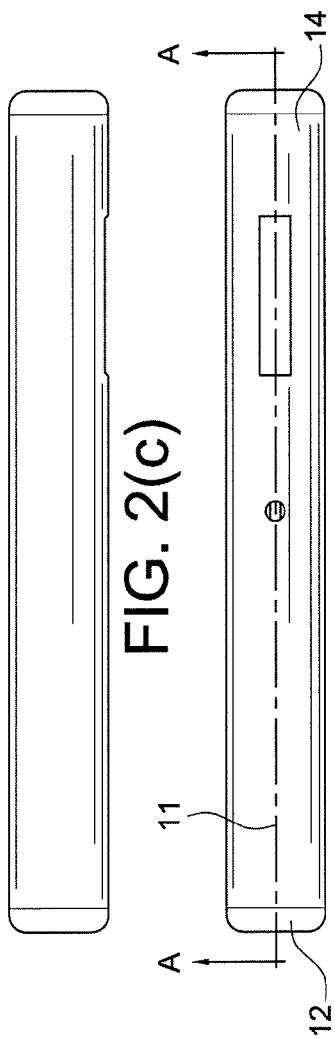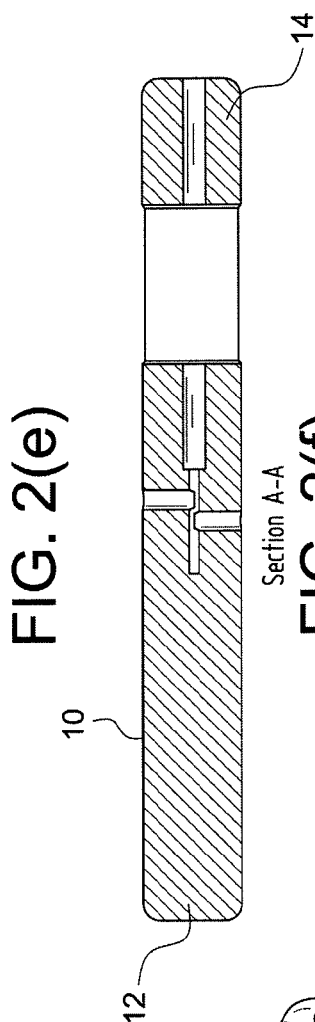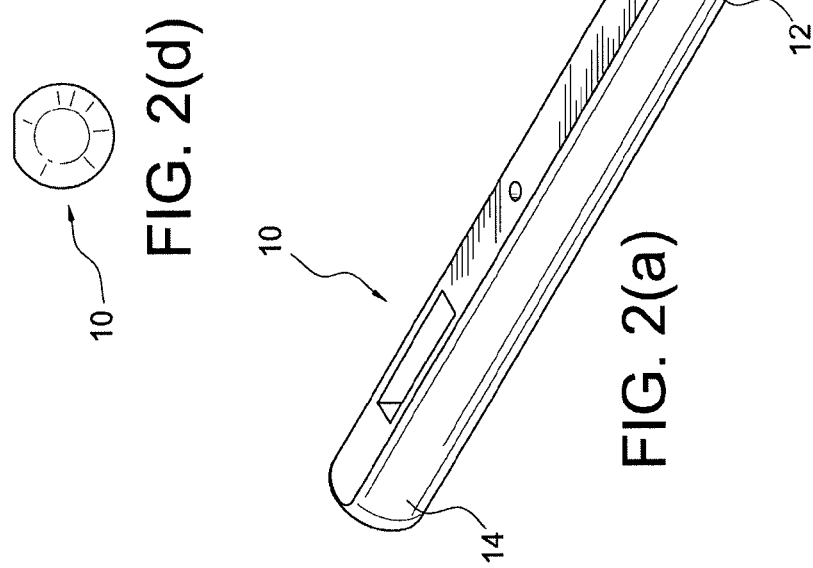

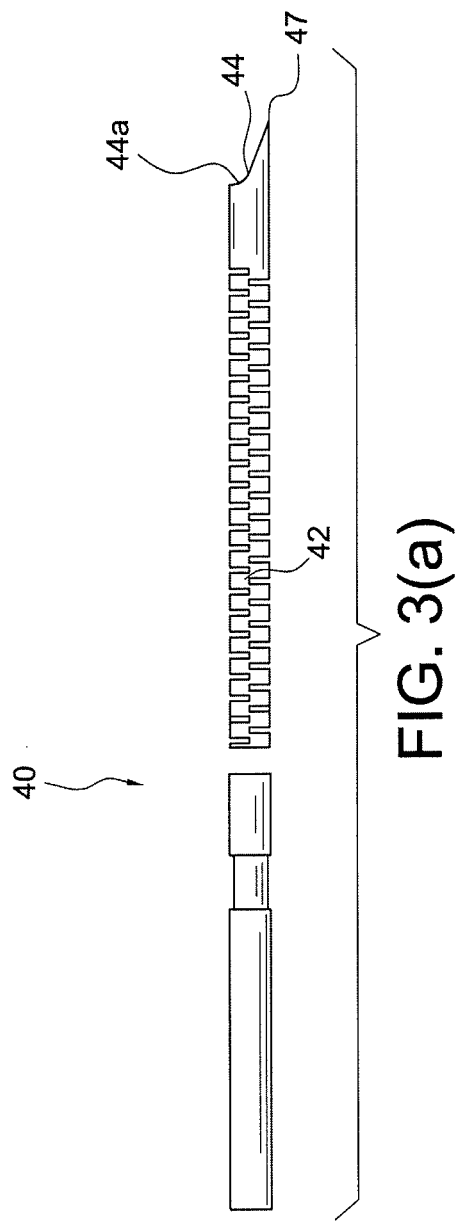
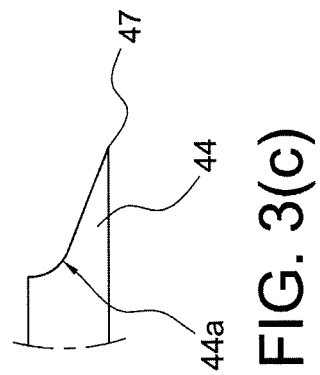
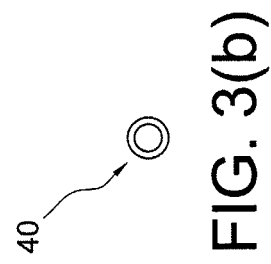
FIG. 3(a)
FIG. 3(c)
FIG. 3(b)

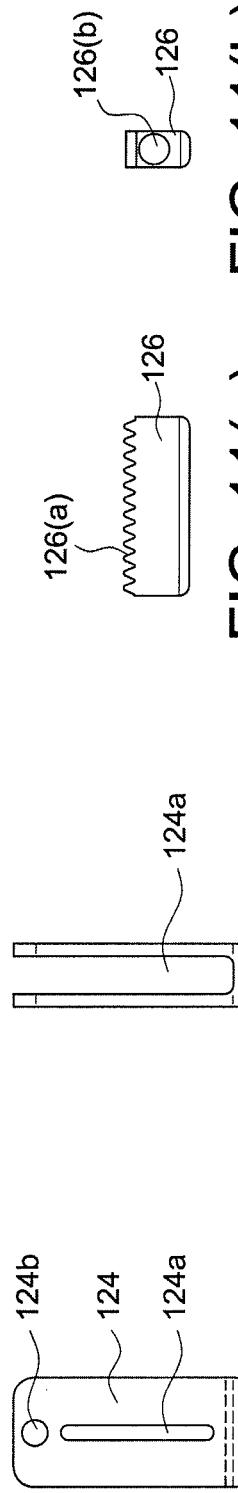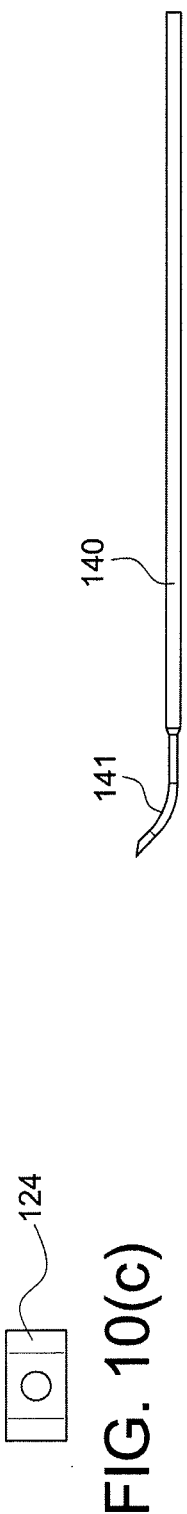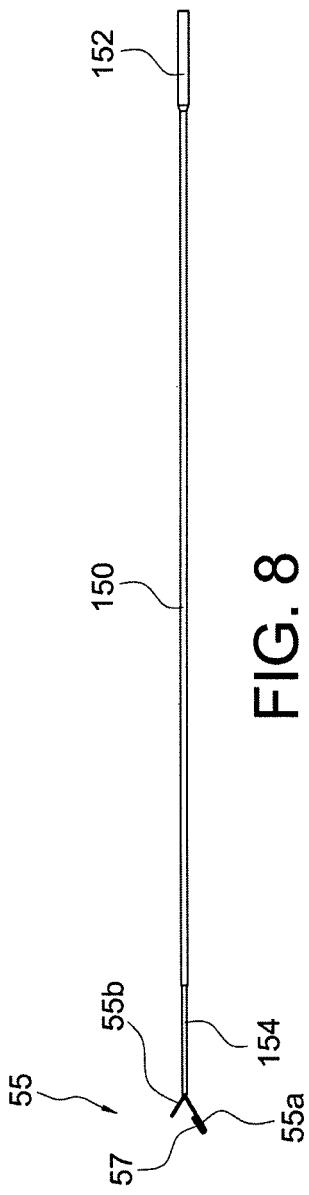

SUTURE SNARE WITH RETRACTABLE SLEEVE

CROSS-REFERENCE TO RELATED APPLICATIONS

This application claims the benefit of U.S. Provisional Application No. 61/723,493 filed Nov. 7, 2012, the disclosure of which is incorporated by reference in its entirety herein.

FIELD OF THE INVENTION

The present invention relates to surgical devices and, more particularly, to a surgical instrument for suturing of tissue during surgery.

BACKGROUND OF THE INVENTION

Surgical procedures often require sutures to ligate, join or otherwise treat tissue. Generally, suture needles with attached suture strands are grasped either manually or by forceps and passed through the desired work site so a knot can be tied. While the procedures are fairly uncomplicated in open surgery where most suture sites are readily accessible, in endoscopic procedures, where access to the work site is not readily available, the surgeon must use auxiliary devices to grasp the suture strands and pass them through desired tissue.

Various instruments and techniques have been developed and are known for surgical repairs requiring the passing of sutures to distant locations. Certain suture passers deploy a suture snare within the joint space during arthroscopic surgery. Due to the limited space within the joint, deployment of the snare is often challenging. A suture passer (snare) with reduced space requirement for the device is needed. Also needed are improved devices and techniques that enable the surgeon to pass sutures arthroscopically to an internal body part where the work site is only accessible through a small portal or cannula and it is difficult to pass sutures within the body.

SUMMARY OF THE INVENTION

The present invention provides a delivery device (suture passer or suture snare) that may be used in both open and endoscopic surgical procedures and that is designed with an internal/inner member and a retractable outer sheath (sleeve). The device is passed through tissue, and the outer sheath is retracted, allowing the snare to open. The suture is captured by the snare, and the outer sheath is then released so that it returns to its distal position, closing the snare and securing the captured suture. Since the snare is exposed by retracting the outer sheath (sleeve), rather than advancing the snare, the space requirement for the device is reduced, as is the possibility that the snare will undesirably contact sensitive tissue.

The present invention also provides a method of retrieving at least one flexible strand (for example, suture) by inter alia (i) providing a delivery device with a handle, an internal member and an actuating retractable outer sheath attached to the handle; (ii) providing the device in the vicinity of the flexible strand (suture) to be retrieved; (iii) retracting the outer sheath to expose at least a part of the internal member and to open a grasping element (snare) of the inner member; (iv) capturing the flexible strand (suture) with the grasping element (snare); and (v) releasing the outer sheath so that it returns to its distal position in which it covers the snare and secures the captured flexible strand (suture).

The present invention also provides a method of passing/deploying at least one flexible strand (for example, suture) by inter alia (i) providing a delivery device with a handle, a flexible internal member terminating with a grasping element (snare) and a rigid outer sheath attached to the handle; (ii) loading the delivery device with the at least one flexible strand (at least one suture) by securing the at least one flexible strand to the grasping element; (iii) passing the delivery device loaded with the at least one flexible strand through or around tissue (for example, soft tissue); and (iv) retracting the outer sheath to expose at least a part of the flexible internal member and to open the grasping element (snare) of the inner member, to release the at least one flexible strand.

These and other features and advantages will be more apparent from the following detailed description that is provided in connection with the accompanying drawings and illustrated exemplary embodiments.

BRIEF DESCRIPTION OF THE DRAWINGS

FIG. 1 illustrates an exploded view of a suture passing device (suture passer) according to a first embodiment of the present invention (showing a handle, a sleeve, an inner shaft, a thumb trigger and a spring).

FIG. 2(a) illustrates a perspective view of the handle of the suture passing device of FIG. 1.

FIG. 2(b) illustrates a top view of the handle of FIG. 2(a).

FIG. 2(c) illustrates a top view of the handle of FIG. 2(a).

FIG. 2(d) illustrates a side view of the handle of FIG. 2(a).

FIG. 2(e) illustrates a partial cross-sectional top view of the handle of FIG. 2(a).

FIG. 2(f) illustrates a cross-sectional view of the handle of FIG. 2(e) taken along line A-A of FIG. 2(e).

FIG. 3(a) illustrates a front view of the outer sleeve (with a flexible i.e., laser cut region) of the suture passing device of FIG. 1.

FIG. 3(b) illustrates a side view of the outer sleeve of FIG. 3(a).

FIG. 3(c) illustrates an enlarged view of the distal tip of the outer sleeve of FIG. 3(a).

FIG. 8 illustrates a side view of the inner shaft of the suture passing device of FIG. 5.

FIG. 9 illustrates a side view of the outer sleeve (sheath) of the suture passing device of FIG. 5.

FIG. 10(a) illustrates a front view of the pinion housing of the actuator mechanism of the suture passing device of FIG. 5.

FIG. 10(b) illustrates a lateral view of the pinion housing of FIG. 10(a).

FIG. 10(c) illustrates a top view of the pinion housing of FIG. 10(a).

FIG. 11(a) illustrates a front view of the rack of the actuator mechanism of the suture passing device of FIG. 5.

FIG. 11(b) illustrates a side view of the rack of FIG. 11(a).

DETAILED DESCRIPTION OF THE PREFERRED EMBODIMENTS

Figure 4A:
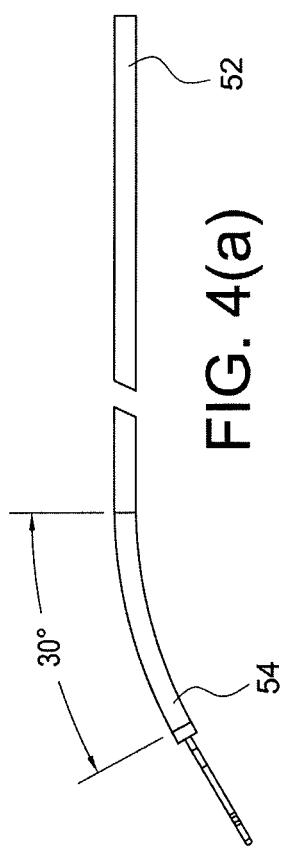
FIG. 4(a) illustrates a top view of the inner shaft of the suture passing device of FIG. 1.
Figure 4B:
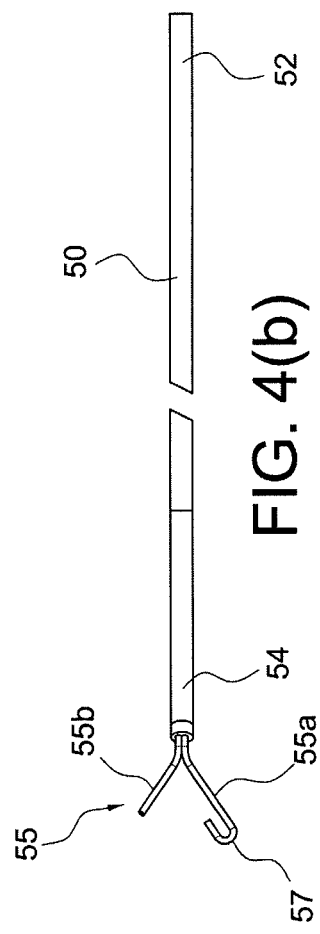
FIG. 4(b) illustrates a lateral perspective view of the inner shaft of FIG. 4(a) in the open or exposed position.
Figure 4C:
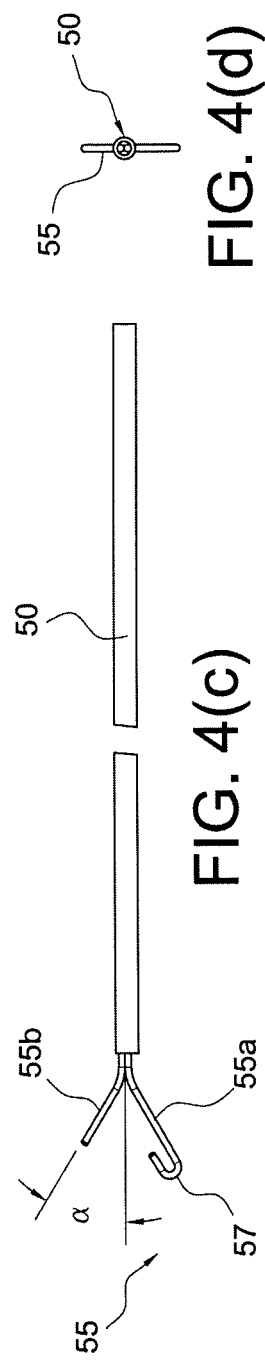
FIG. 4(c) illustrates a lateral view of the inner shaft of FIG. 4(b).
Figure 4D:
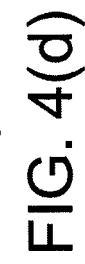
FIG. 4(d) illustrates a side view of the inner shaft of FIG. 4(b).

The present invention provides delivery devices (suture passers or suture manipulating instruments) for use in both open and endoscopic surgical procedures that are designed to reduce the space requirement for these devices. The suture passers are provided with an outer sheath (sleeve) that is retractable to permit exposing (opening) of a grasping mechanism (suture grasping mechanism) located at a distal end of an inner shaft.

Once the device is passed through tissue, the outer sheath is retracted allowing the snare to open. The suture is captured by the snare, and the outer sheath is then released so that it returns to its distal position, closing the snare and securing the captured suture. Since the snare is exposed by retracting the outer sheath (sleeve), rather than advancing the snare, the space requirement for the device is reduced, as is the possibility that the snare will undesirably contact sensitive tissue.

A method of retrieving at least one flexible strand (for example, suture) comprises inter alia the steps of: (i) providing a delivery device with a handle, an internal/inner member and an actuating retractable outer sheath attached to the handle; (ii) providing the device in the vicinity of the at least one flexible strand (suture) to be retrieved; (iii) retracting the outer sheath to expose at least a part of the inner member and to open a grasping element (snare) of the inner member; (iv) capturing the at least one flexible strand (suture) with the grasping element (snare); and (v) releasing the outer sheath so that it returns to its distal position in which it covers the snare and secures the captured flexible strand (suture).

A method of passing/deploying at least one flexible strand (for example, suture) comprises inter alia the steps of: (i) providing a delivery device with a handle, a flexible internal member terminating with a grasping element (snare), and a rigid outer sheath attached to the handle; (ii) loading the delivery device with the at least one flexible strand (at least one suture) by securing the at least one flexible strand to the grasping element; (iii) passing the delivery device loaded with the at least one flexible strand through or around tissue (for example, soft tissue); and (iv) retracting the outer sheath to expose at least a part of the flexible internal member and to open the grasping element (snare), to release the at least one flexible strand.

Referring now to the drawings, where like elements are designated by like reference numerals, FIGS. 1-4(d) illustrate suture passing device 100 (suture snare assembly 100) according to a first exemplary embodiment of the present invention. FIGS. 5-13 illustrate suture passing device 200 (suture snare assembly 200) according to a second exemplary embodiment of the present invention. FIGS. 14-19 illustrate exemplary steps of a method of retrieving (capturing/delivering/manipulating) a flexible strand with the suture passing device 200.

FIGS. 1-4(d) illustrate suture passing instrument or device 100 that includes handle assembly 10 which has a proximal end 12 and a distal end 14, and a longitudinal axis 11. Device 100 further includes an outer, flexible sleeve or sheath 40, and a rigid inner shaft 50 connected to the distal end 14 of the handle 10. Device 100 further includes an actuator 20 (for example, a thumb trigger 20) and a spring 22.

As detailed below, the actuator (thumb trigger) 20 is actuated to retract the flexible outer sheath 40, to open a suture grasping mechanism (snare) 55 located at a most distal end of the rigid inner shaft 50. The actuator 20 is actuated between a first position (when the actuator is closest to the distal end 14, and when the outer sleeve 40 is not retracted, snare is enclosed) and a second position (when the actuator is closest to the proximal end 12, and when the outer sleeve 40 is retracted, snare is open). The actuator 20 is mounted on handle 10 so as to slide in a direction about parallel to the longitudinal axis 11 of the handle 10, for example, in the direction of arrow A shown in FIG. 1. A member of the actuator 20 is connected to the outer sheath 40 to operate retraction of the sheath also in the direction of arrow A. The actuator 20 is spring loaded in the first (non-retracted) position. Optionally, the actuator could be provided with two discrete locking positions or multiple positions.

FIGS. 2(a)-(f) illustrate various views of the handle 10 of suture passer 100. FIGS. 3(a)-(c) and FIGS. 4(a)-(d) illustrates various views of the outer sleeve (sheath) 40 and inner shaft 50, respectively.

As shown in FIGS. 3(a)-(c), the outer sleeve (sheath) 40 extends away from the distal end 14 and terminates in tip 44. The edges 44a of the open distal end are sharpened, coming to a point 47 at the most distal edge to allow sleeve 40 to penetrate tissue. The sleeve (sheath) 40 also includes a flexible/bendable region 42 (for example, a laser cut region 42 or wire cut, or formed by any other operation to make the tube flexible) that provides flexibility to the sleeve 40. The flexible region allows the sleeve to retract around the bend of the inner shaft. Flexible/bendable region 42 of the sleeve is the length of the bend region of the inner shaft plus the distance that needs to be retracted to expose the snare. In other embodiments, the flexible region may extend from about half the length of the sleeve (sheath) 40 to the entire length of the sleeve.

The outer sleeve (sheath) 40 is retractable. Once device 100 is passed through tissue, the sheath 40 is retracted (by actuating thumb trigger 20) to expose and open suture grasping mechanism (snare) 55 of the inner, rigid shaft 50.

FIGS. 4(a)-(d) illustrate various views of inner shaft 50 of device 100. Inner shaft 50 is preferably a fixed, rigid, internal member provided with a proximal end 52 (that abuts the handle 10) and a distal end 54 that terminates with a suture grasping mechanism or snare 55. A bend region is formed near the distal end of the inner shaft. The bend region may be a fixed/solid region and may have a single angle in the range of 10 to 75 degrees or a compound angle or a helix, or may have left and right orientations. As shown in FIGS. 4(a)-(d), the suture grasping mechanism (snare) 55 is formed of two segments, for example, two wire-like members 55a, 55b. In an exemplary-only embodiment, one of the segments (for example, member 55a) may have a U-shaped configuration (i.e., may be provided with a U-shaped hook element 57) while the other segment (for example, member 55b) may have a straight configuration and a length shorter than that of the other segment.

When the outer sheath 40 is retracted, the two segments of the suture grasping mechanism 55 are exposed and open such that segment 55b extends away from segment 55a, as shown in FIGS. 4(a)-(d) (to allow capturing of suture in the U-shaped hook 57). The angle α is at its greatest when the outer sheath is retracted. When the outer sheath is allowed to return to its original position, the angle between the segments 55a and 55b is reduced, for retaining the suture between the segments and within the outer sleeve. The angle α between the segments 55a and 55b can be in the range of 10 to 180 degrees or between the longitudinal axis of the inner shaft and one member the range would be 5 to 90 degrees.

Although the suture grasping mechanism (snare) 55 was detailed above as being formed of two segments, i.e., members 55a and 55b, the invention is not limited to this exemplary-only embodiment and contemplates embodiments wherein the suture snare (the grasping mechanism) has any form and configuration and any number of members. For example, the invention also contemplates a suture snare or suture retriever formed of only one segment, for example, one member that may have a U-shaped or curved configuration, without the addition of a second limb.

An exemplary method of endoscopically retrieving at least one flexible strand (for example, at least one suture) with instrument 100 of the present invention comprises the steps of inter alia: (i) providing a suture passer 100 with a handle 10, and a fixed rigid internal member 50 and an actuating flexible outer sheath 40, both attached to the handle 10; (ii) providing the suture passer 100 in the vicinity of suture to be retrieved; (iii) actuating (retracting) the outer sheath 40 to expose at least a part of the fixed rigid internal member 50 and to open the suture grasping element (the snare) 55; (iv) engaging a suture with the suture grasping element (snare) 55; and (v) releasing the outer sheath 40 so that it returns to its distal position to close the suture grasping element (the snare) 55 and secure the captured suture.

An exemplary method of passing/deploying at least one flexible strand (for example, suture) with instrument 100 of the present invention comprises inter alia the steps of: (i) providing a delivery device 100 with a handle 10, a flexible internal member 50 terminating with a grasping element 55 (snare 55), and a rigid outer sheath 40 attached to the handle 10; (ii) loading the delivery device with the at least one flexible strand 70 (at least one suture 70) by securing the at least one flexible strand 70 to the grasping element 55; (iii) passing the delivery device 100 loaded with the at least one flexible strand 70 through or around tissue (for example, soft tissue); and (iv) retracting the outer sheath 40 to expose at least a part of the flexible internal member 50 and to open the grasping element 55 (snare 55), to release the at least one flexible strand 70.

FIGS. 5-19 illustrate exemplary suture passing instrument 200 according a second embodiment of the present invention. The overall instrument function of suture passer 200 is about similar to that of instrument 100, however the actuation mechanism is changed.

When a surgeon uses suture passers in arthroscopic surgery, such as suture passer 100 detailed above, the motion of the instrument pictured on the screen is often different from what the surgeon's hands are doing. This aspect can be potentially confusing for the surgeon if the relative motion of the surgeon's hand is opposite to what the surgeon sees on the screen. This is especially true for the retrograde suture passer device 100, as the relative motion between the shaft and handle can make it appear that the snare is deploying while looking through an arthroscope. For this reason, suture passer 200 of the present invention (detailed below) was developed to address the potential "confusion" of the surgeon, i.e., to reverse the action of the actuator to avoid any potential confusion.

As explained in more detail below, the suture snare assembly 200 (suture passer 200) includes a new actuation method, and new actuation mechanism or actuator assembly, that utilizes a rack and pinion setup, where the pinion is manipulated so that, when rotated in the "forward" direction, the linear "rack" which is connected to the shaft moves "backwards" relative to the motion of the surgeon's thumb (in a reversed position). This is a result of changing from rotational to linear motion.

As also detailed below, the suture snare assembly 200 (suture passer 200) is also provided with a novel locking mechanism that provides the instrument with discrete locking positions (i.e., with one or more locking positions, for example, three different discrete locking positions). To accomplish this, and as detailed below, the "pinion" gear is designed to be able to translate up and down relative to the shaft via slots in the associated housing. A slot located in the gear allows a stationary pin to slide while the gear is rotating. When the device needs to be locked, the pressure on the pinion is released, and a return spring pushes the housing back up, and the pin finds its way into detents located in the slot on the pinion. However, the return of the gear is not enough to fully disengage the teeth, and since the gear can no longer rotate, the shaft can no longer translate, essentially locking the shaft in position.

To adjust the locking positions with the novel mechanism of the present invention, one could simply calculate the angles in which to place the detents via simple geometry. Because the gear is a set radius, one can calculate how far the linear travel of the actuator will be by simply converting the linear distance required to a percentage of the circumference, and then converting that percentage back into degrees. A general equation for this process is equation (1) below:

$$\text{Length} = (\text{angle}/360) * 2\pi * r \qquad \text{Equation (1):}$$

where Length is the distance between the two locking points, and r is the radius.

FIGS. 5-13 illustrate suture passing instrument or device 200 (suture snare assembly 200) that includes a handle assembly 110 which has a proximal end 112 and a distal end 114, and a longitudinal axis 111. Device 200 further includes an outer sleeve or sheath 140 that houses an inner shaft 150 (inner member 150) connected to the distal end 114 of the handle 110. Device 200 further includes an actuator 120 mounted on and/or within the handle 110.

Figure 5:
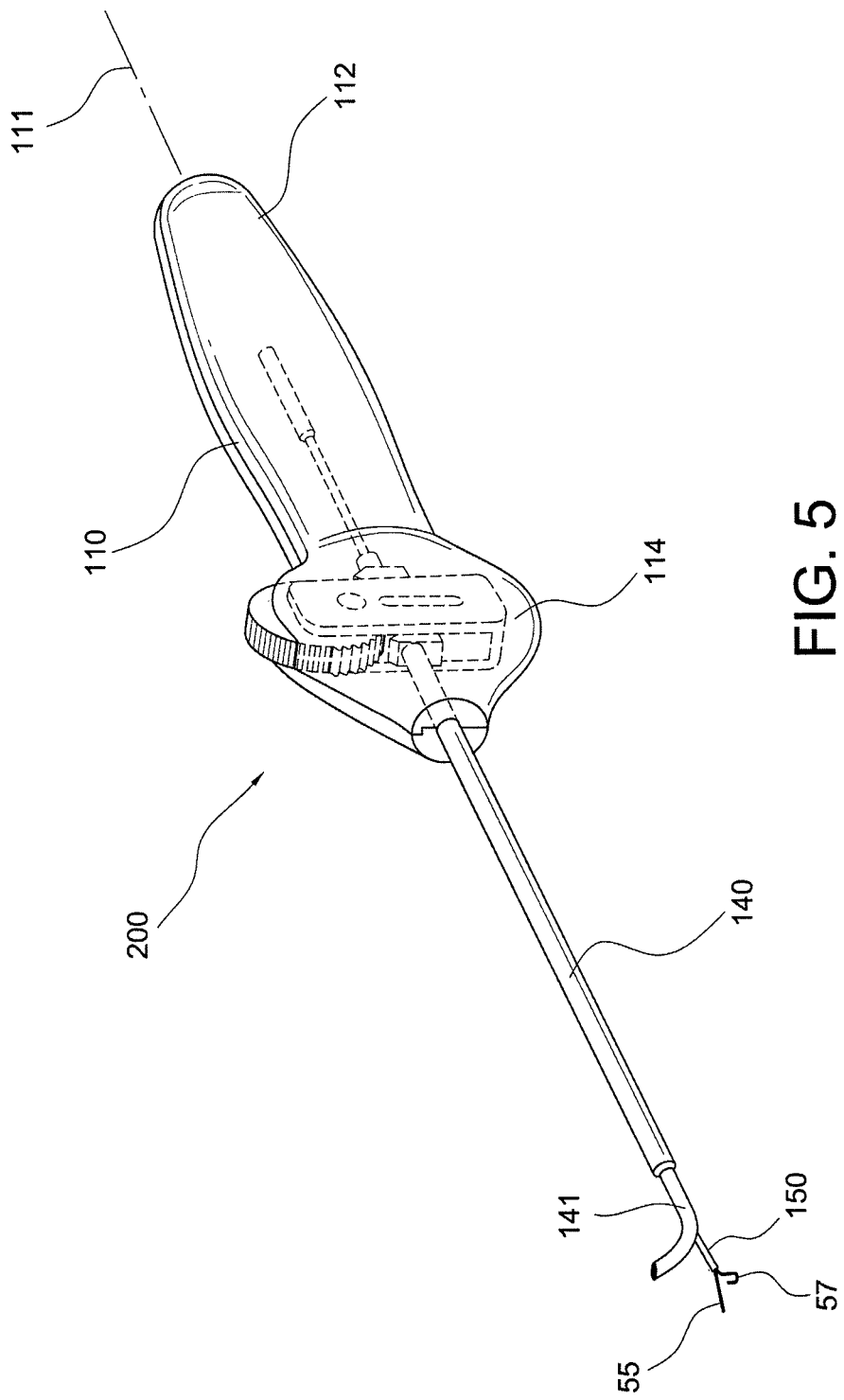
FIG. 5 illustrates a perspective view of a suture passing device (suture passer) according to a second embodiment of the present invention.
Figure 6:
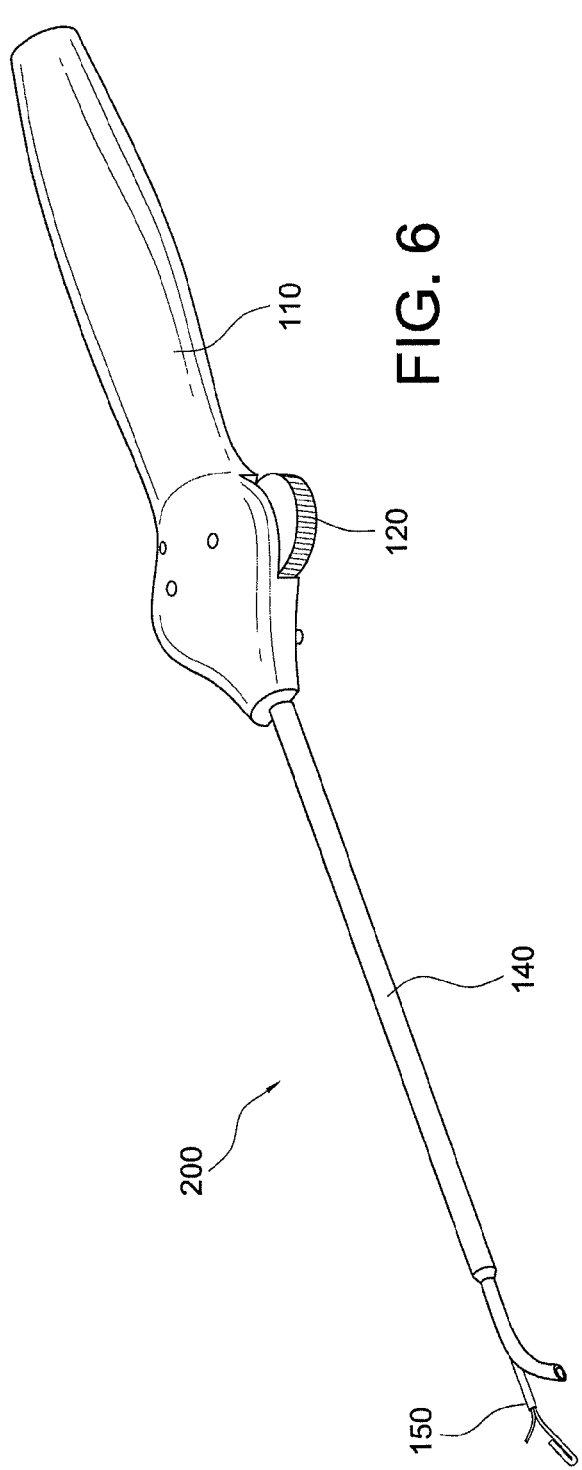
FIG. 6 illustrates an isometric view of the suture passing device of FIG. 5.
Figure 7:
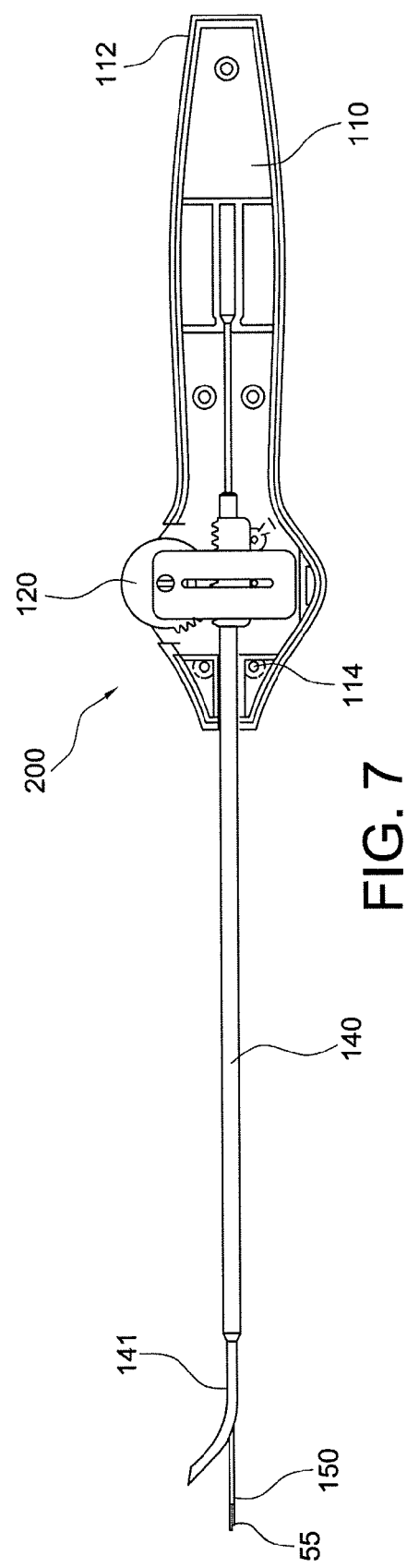
FIG. 7 illustrates a partial cross-sectional view of the suture passing device of FIG. 5.

Preferably, the outer sleeve or sheath 140 is rigid (solid) and curved at its most distal end (i.e., at distal region 141 as shown in FIGS. 5 and 9, for example). The curved/bend region is formed at the distal end of the sheath and may have a single angle in the range of 10 to 75 degrees, or a compound angle or a helix, or may have left and right orientations.

Preferably, the inner shaft 150 is flexible and is housed by the outer sleeve or sheath 140. As in the previously-described embodiment, and as shown in FIG. 8, for example, the internal member 150 provided with a proximal end 152 (that abuts the handle 110) and a distal end 154 that terminates with a suture grasping mechanism or snare 55. As detailed above, the suture grasping mechanism (snare) 55 is formed of two exemplary segments, for example, two wire-like members 55a, 55b (FIG. 8); however, suture grasping mechanism 55 may also consist of only one member. In an exemplary-only embodiment, one of the segments (for example, member 55a) may have a U-shaped configuration (i.e., may be provided with a U-shaped hook element 57) while the other segment (for example, member 55b) may have a straight configuration and a length shorter than that of the other segment.

When the outer sheath 140 is retracted, the two segments of the suture grasping mechanism 55 are exposed and open such that segment 55b extends away from segment 55a, as shown in FIGS. 5 and 8 (to allow capturing of suture in the U-shaped hook 57).

Reference is now made to FIGS. 10(*a*)-13(*b*) which illustrate details of actuation mechanism 120 of the second embodiment of the present invention. As shown in the exploded view of FIG. 12, actuation mechanism or assembly 120 includes a pinion 122 (pinion gear or circular gear 122) with a circular pitch and plurality of teeth 122a, a pinion housing 124, a rack 126 (linear bar or gear rack 126) with a linear pitch and a plurality of teeth 126a, and three exemplary alignment and locking pins 135, 136, 137. Rotational motion is applied to the stationary pinion gear 122, which causes the gear rack 126 to move. Thus, the rotational movement of the pinion gear 122 is transferred to the linear motion of the gear rack 126. The teeth on the linear rack have the same pitch as those of the pinion gear.

Figure 13A:
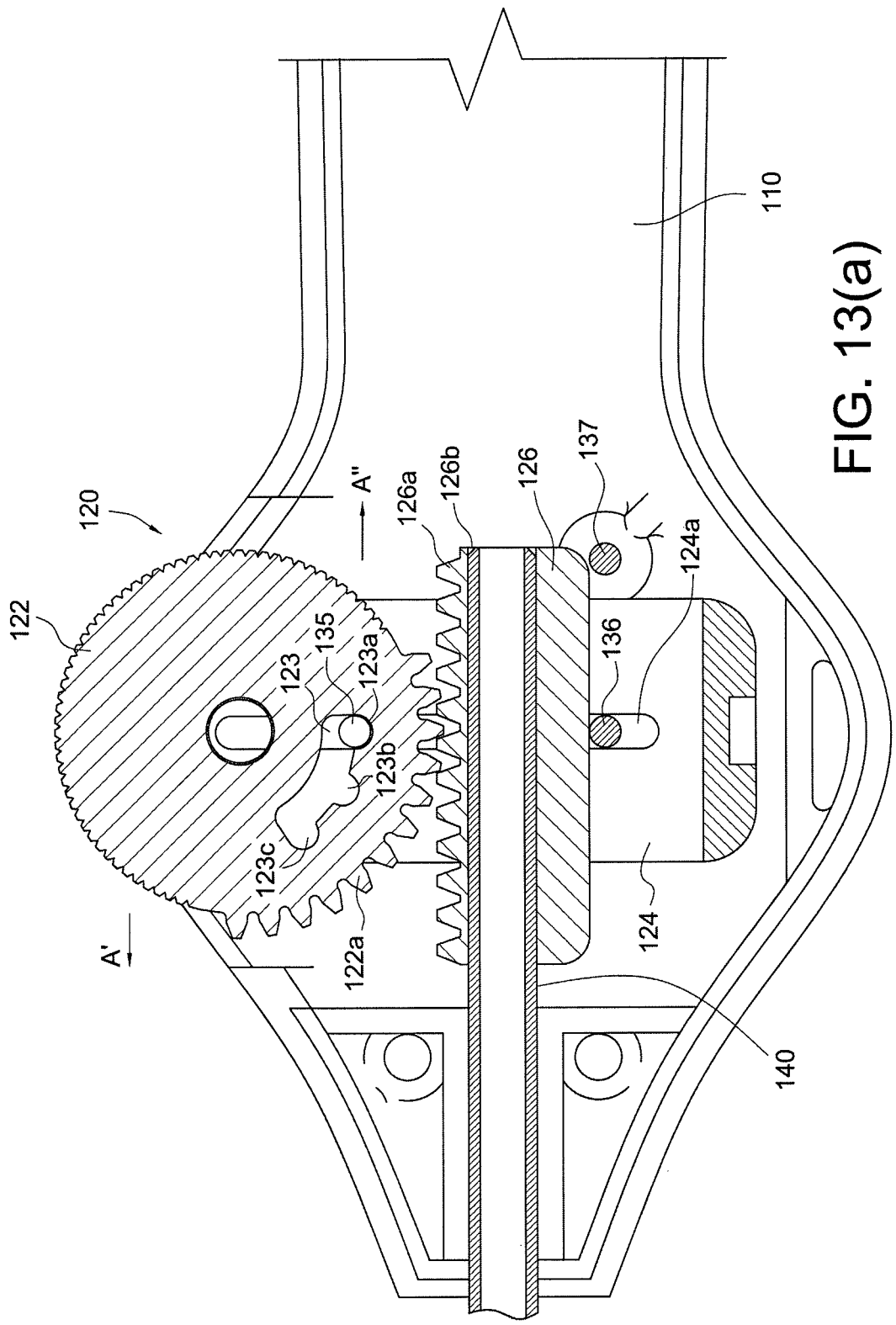
FIG. 13(a) is an enlarged view of the actuating mechanism of the suture passing device of FIG. 5, at a first position (with the sheath non-retracted).
Figure 13B:
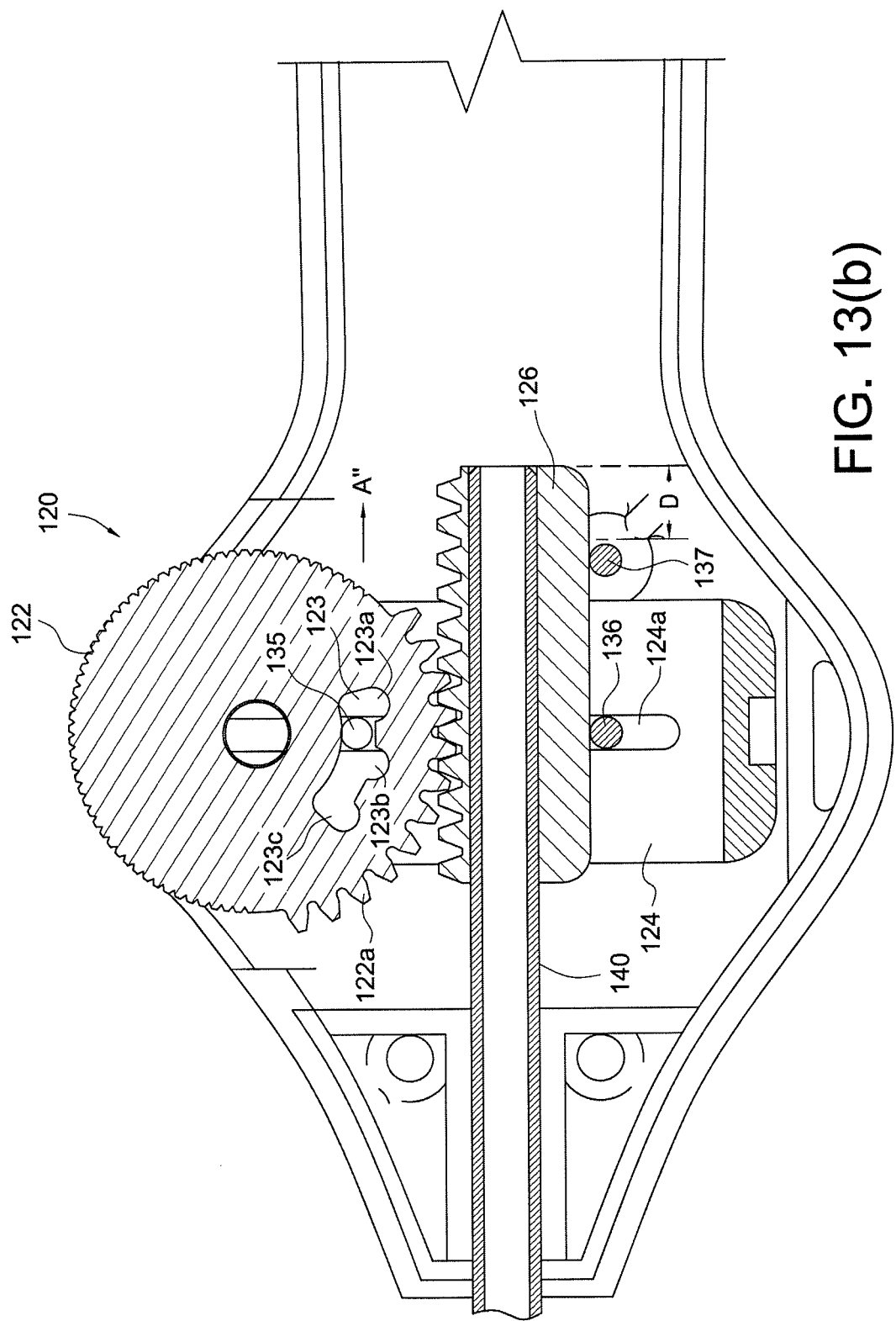
FIG. 13(b) is an enlarged view of the actuating mechanism of the suture passing device of FIG. 5, at a second position (with the sheath retracted).
Figure 14:
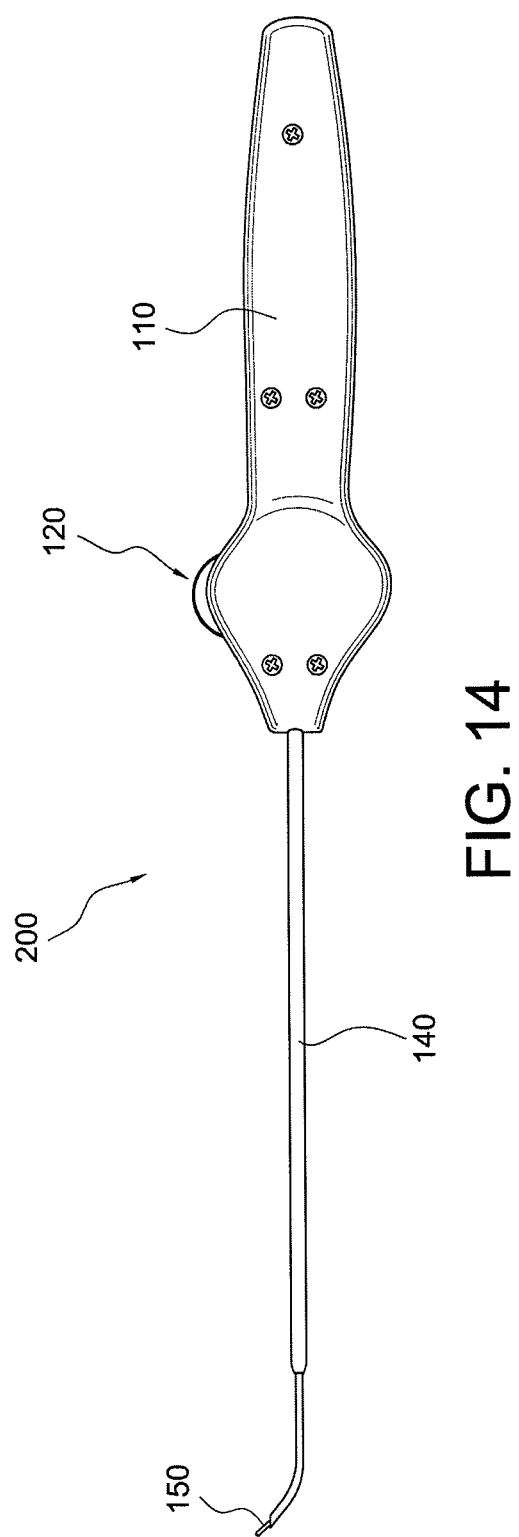
FIGS. 14-19 illustrate subsequent steps of a method of manipulating suture (grasping and delivering) with the suture passing instrument of FIG. 5.
Figure 15:
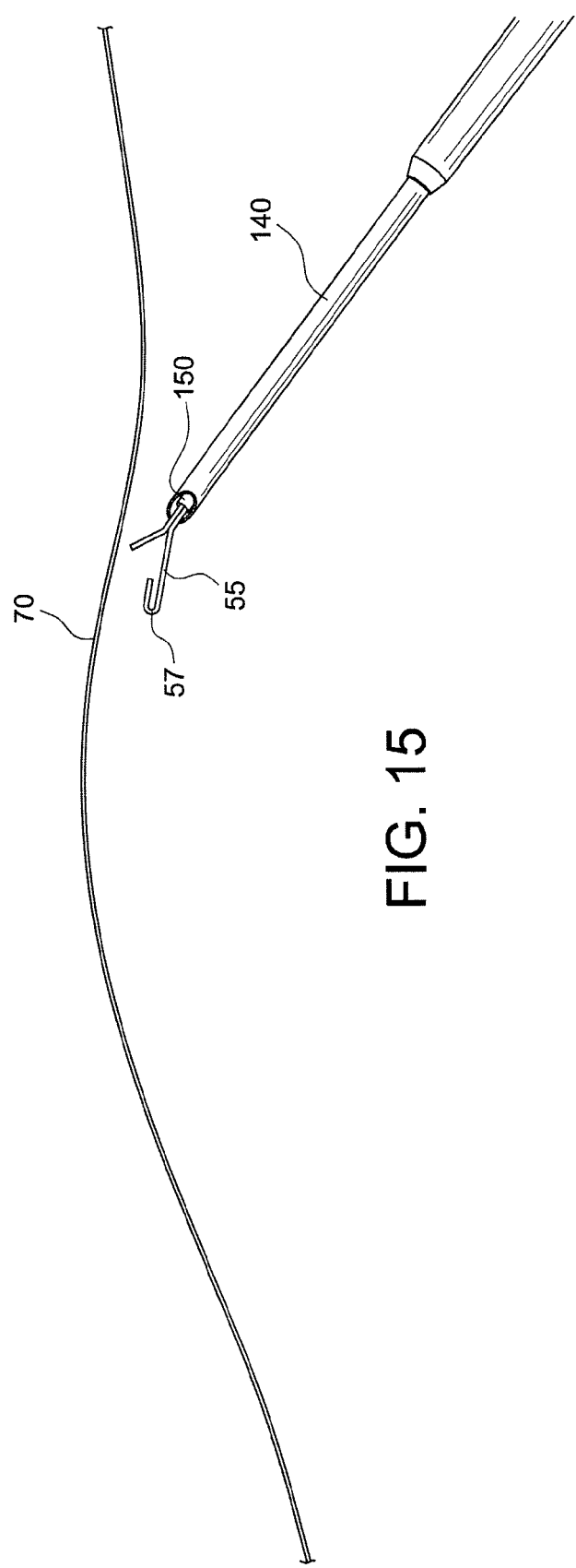
Figure 16:
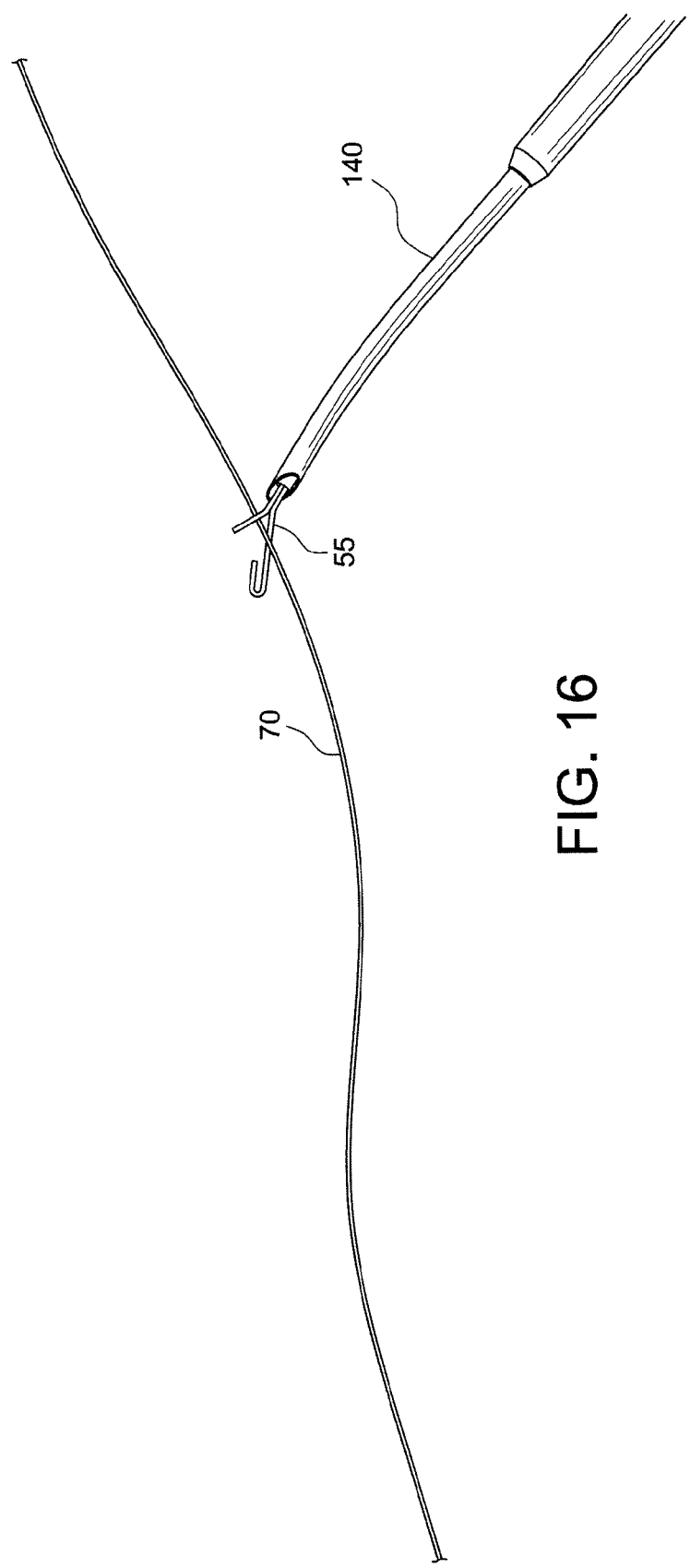
Figure 17:
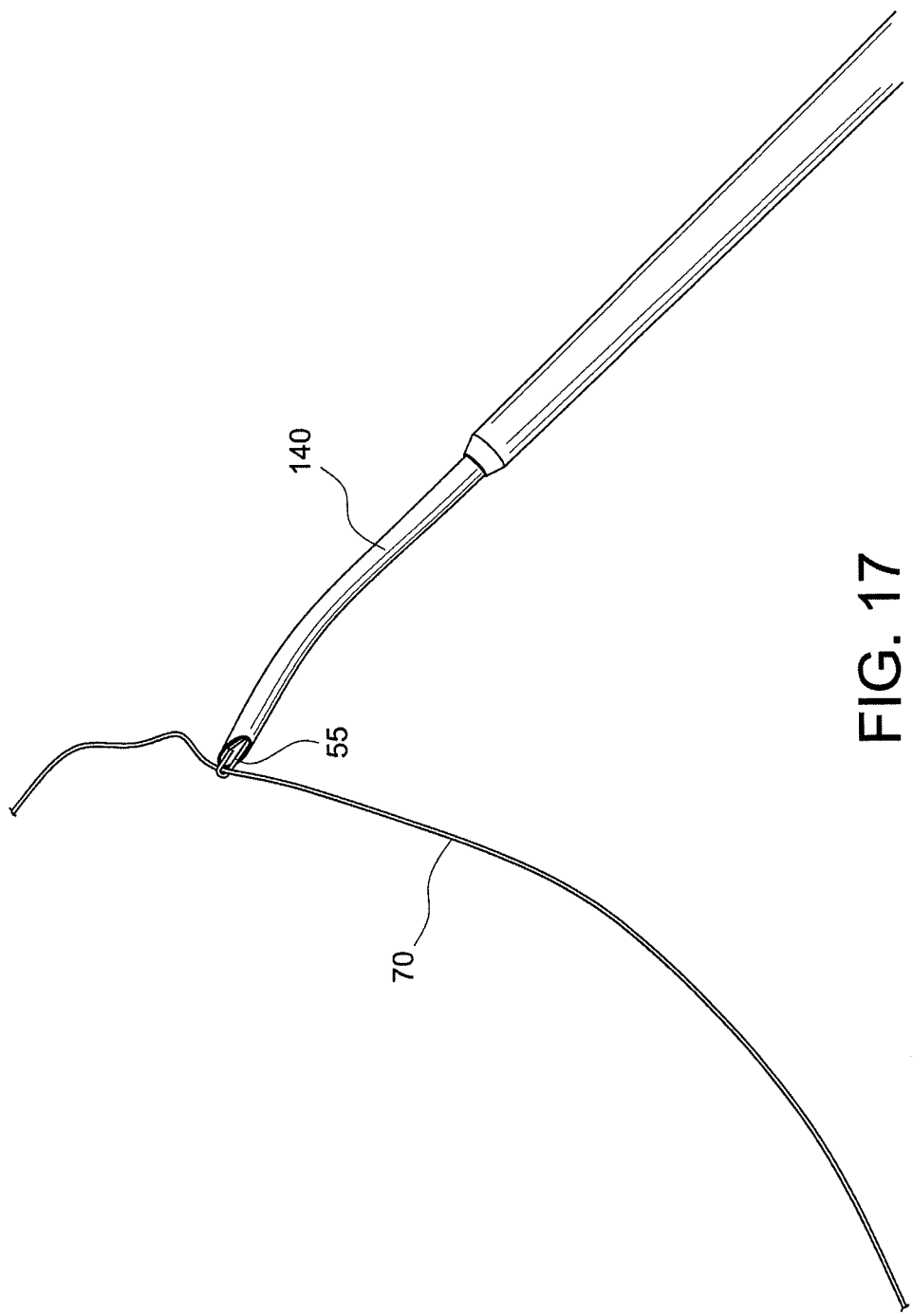
Figure 18:
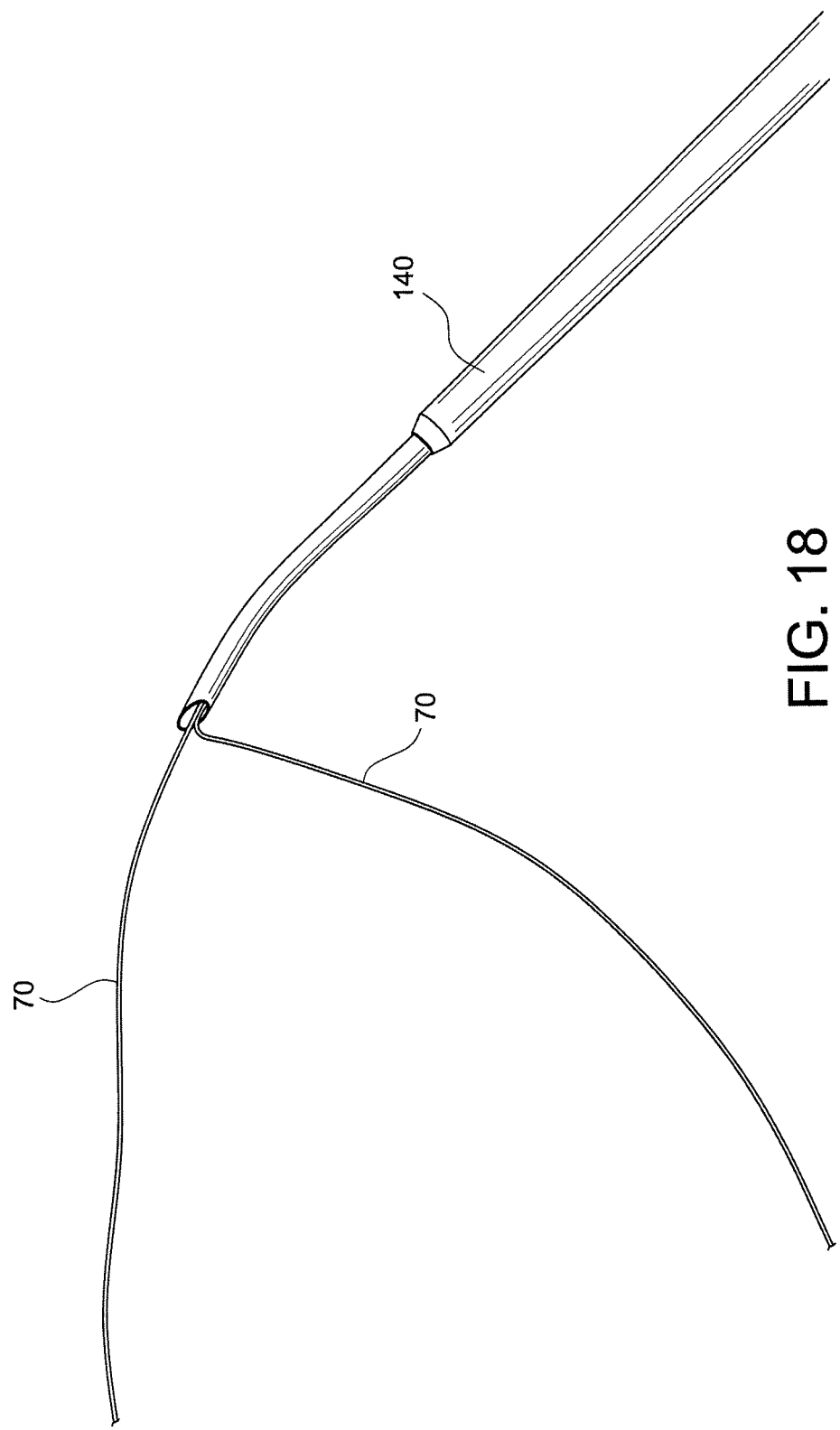
Figure 19:
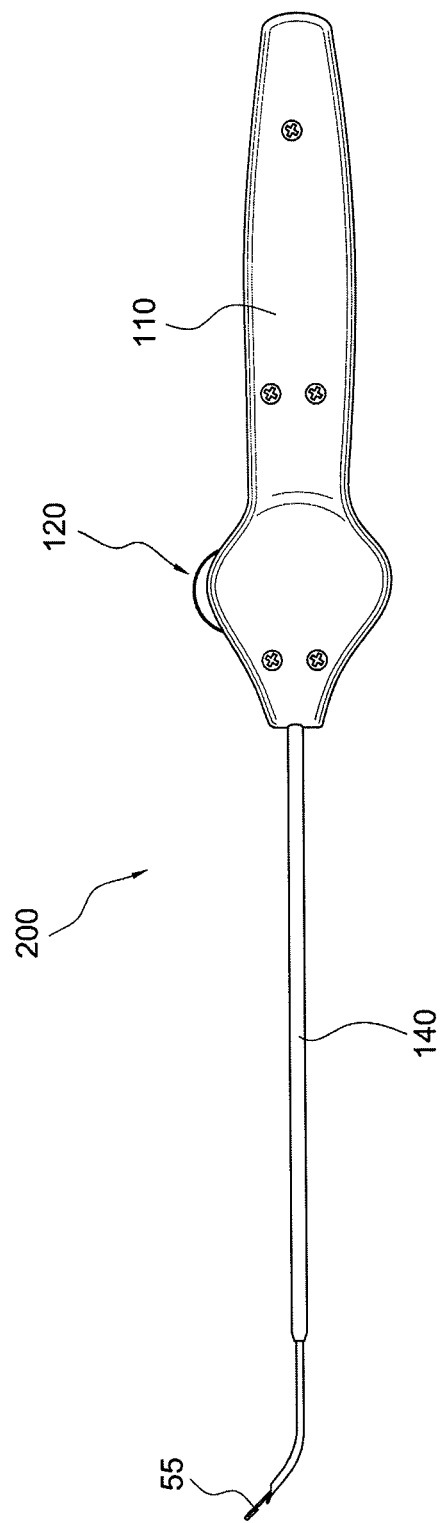

During assembly, the sheath 140 is inserted within channel 126b of the rack 126 and pinion housing 124, and securely engaged by the rack 126. As shown in FIGS. 13(*a*) and 13(*b*), rotation of the pinion 122 along the direction of arrow A' in a forward direction (FIG. 13(*a*)) causes the rack 126 that securely engages sheath 140 to move linearly for a distance D in the direction of arrow A" (FIG. 13(*b*)) and, in turn, to retract/move back the sheath 140 to expose snare 55. Rotational motion is applied to the stationary pinion gear 122, which causes the gear rack 126 and the sheath 140 to move. Thus, the rotational movement of the pinion gear 122 is transferred to the linear motion of the gear rack 126. The teeth 126a on the linear rack have the same pitch as the teeth 122a of the pinion gear 122.

Figure 12:
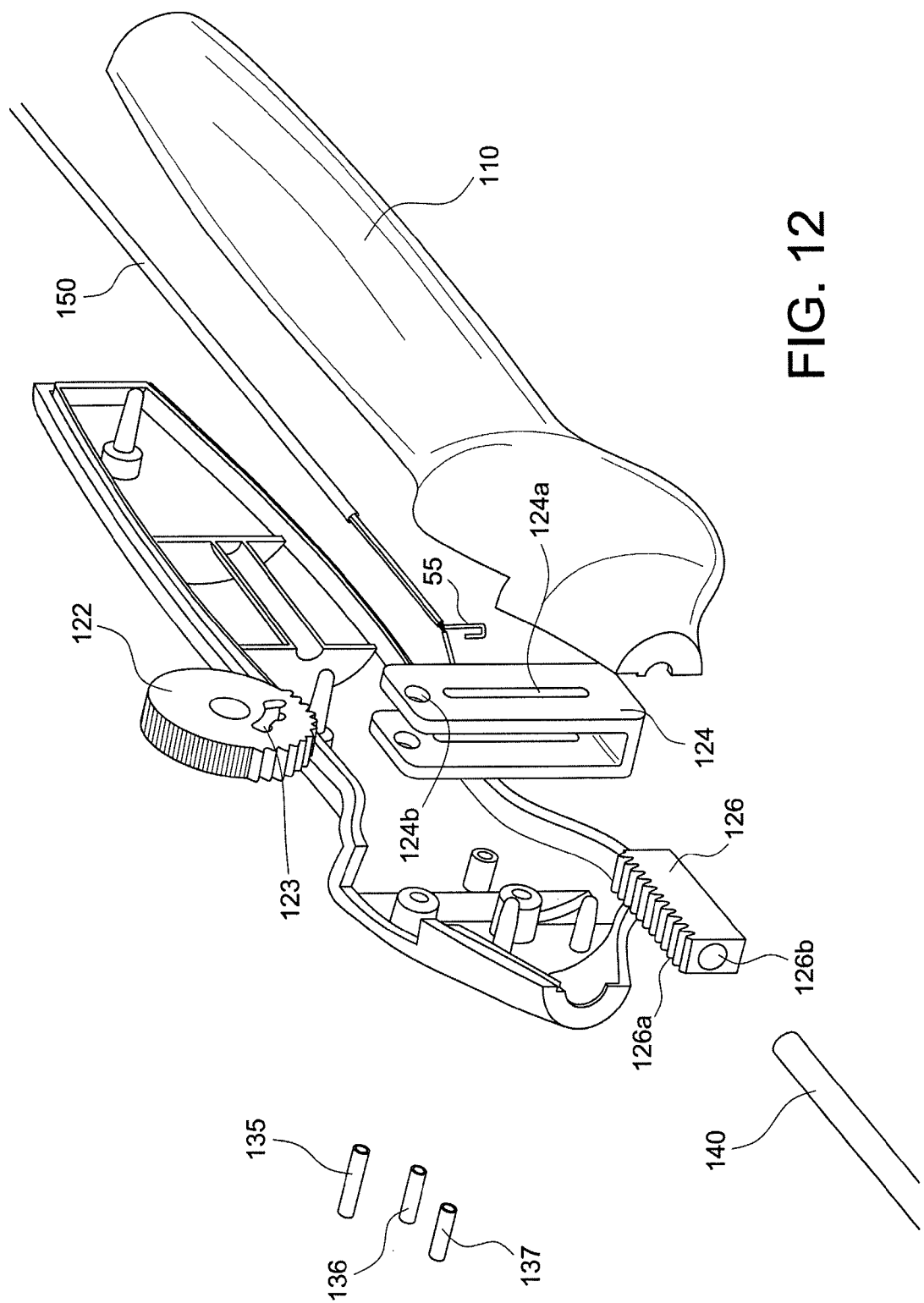
FIG. 12 is an exploded view of the suture passing device of FIG. 5.

Pinion housing 124 of the actuating mechanism 120 is provided with a plurality of transversal elongated slots 124a and a plurality of circular slots 124b, shown in more details in FIG. 12 and FIGS. 10(*a*)-(*c*). The design of the pinion housing 124 allows discrete locking positions, i.e., exemplary three different discrete locking positions, of the actuation mechanism 120. To accomplish this, the pinion gear 122 is designed to be able to translate up and down relative to the shaft 140 via slots 124a, 124b in the associated housing. A slot 123 located in the pinion gear 122 allows stationary/locking pin 135 to slide while the gear 122 is rotating. When the device 200 needs to be locked, the pressure on the pinion 122 is released, and a return spring pushes the housing 124 back up, and the pin 135 finds its way into detents 123a, 123b, 123c located in the slot 123 on the pinion 122. However, the return of the gear 122 is not enough to fully disengage the teeth 122a, and since the gear 122 can no longer rotate, the shaft 140 can no longer translate, essentially locking the shaft 140 in position. As noted above, the embodiment shown in FIGS. 13(*a*) and 13(*b*) illustrate three locking positions (i.e., with slot 123 provided with three exemplary detents 123a, 123b, 123c that accommodate pin 135 at three different locking positions); however, the invention is not limited to this exemplary-only embodiment and contemplates embodiments with the slot 123 provided with any number of detents to allow locking at different discrete positions.

Actuator mechanism 120 (actuating mechanism 120) is actuated to retract the solid/rigid outer sheath 140, to open suture grasping mechanism (snare) 55 located at a most distal end of the flexible inner shaft 150. The actuating mechanism 120 is integrated within the handle 110 so as to allow pushing of pinion 122 in the direction of arrow A' of FIG. 13(*a*) which is about parallel to the longitudinal axis 111 of the handle 110. As detailed above, the actuating mechanism 120 is connected to the outer sheath 140 and operates retraction of the sheath, i.e., movement of the sheath 140 in direction of arrow A" opposite direction of arrow A'. The actuating mechanism 120 is preferably provided with three discrete locking positions provided by the detents 123a, 123b, 123c located in the slot 123 on the pinion 122, for example, a first position (when the outer sleeve 140 is not retracted, and the snare 55 is fully enclosed), a second position (when the outer sleeve 140 is partially retracted, and the snare is exposed but not fully open) and a third position (when the outer sleeve 140 is fully retracted, and the snare is exposed and fully open).

FIGS. 14-19 illustrate subsequent steps of a method of suture manipulating (grasping and delivering) with the suture passing device 200 of the present invention. Once the passing instrument 200 is passed through the tissue, actuation mechanism 120 is actuated to retract outer sheath 140 and to expose the snare (allowing the snare to open). A flexible strand 70 (for example, suture or similar material) is captured by the snare 55, and the outer sheath 140 is then released so that it returns to its distal position, closing the snare 55 and securing the captured strand 70. Since the snare is exposed by retracting the outer sheath (sleeve), rather than advancing the snare, the space requirement for the device is reduced, as is the possibility that the snare will undesirably contact sensitive tissue.

The present invention also provides methods of passing one or more flexible strands through or around tissue and then releasing the passed flexible strands (i.e., deploying the flexible strands), as well as methods of retrieving flexible strands with instrument 200 of the present invention.

An exemplary method of retrieving at least one flexible strand 70 (for example, suture) comprises inter alia the steps of: (i) providing a delivery device 200 with a handle 110, a flexible internal member 150 and a rigid outer sheath 140 attached to the handle; (ii) providing the device 200 in the vicinity of the at least one flexible strand 70 (suture 70) to be retrieved; (iii) retracting the outer sheath 140 to expose at least a part of the flexible internal member 150 and to open a grasping element 55 (snare) of the inner member 150; (iv) capturing the at least one flexible strand 70 (suture 70) with the grasping element 55 (snare 55); and (v) releasing the outer sheath 140 so that it returns to its distal position in which it covers the snare 55 and secures the captured flexible strand 70 (suture 70).

An exemplary method of passing/deploying a flexible strand 70 (for example, suture) through or around tissue comprises inter alia the steps of: (i) providing a delivery device 200 with a handle 110, a flexible internal member 150 terminating with a grasping element 55 (snare), and a rigid outer sheath 140 attached to the handle 110; (ii) loading the delivery device 200 with at least one flexible strand 70 (at least one suture 70) by securing the at least one flexible strand 70 to the grasping element 55; (iii) passing the delivery device loaded with the at least one flexible strand 70 through tissue (for example, soft tissue); and (iv) retracting the outer sheath 140 to expose at least a part of the flexible internal member 150 and to open the grasping element 55 (snare), to release the at least one flexible strand 70.

Flexible strand 70 for use with device 100, 200 may be of any configuration and may comprise any type of material, including suture, suture loops, suture tapes such as FiberTape® suture, FiberWire® suture, shuttle sutures, suturing sutures, among many others. Exemplary flexible strand 70 may be a high-strength suture, such as the high strength suture sold by Arthrex, Inc. of Naples, Fla. under the registered tradename TigerWire® or FiberWire®, which is disclosed and claimed in U.S. Pat. No. 6,716,234, the entire disclosure of which is incorporated by reference in its entirety herewith. FiberWire® suture is formed of an advanced, high-strength fiber material, namely ultrahigh molecular weight polyethylene (UHMWPE), sold under the tradenames Spectra (Honeywell) and Dyneema (DSM), braided with at least one other fiber, natural or synthetic, to form lengths of suture material. The preferred FiberWire® suture includes a core within a hollow braided construct, the core being a twisted yarn of UHMWPE.

The flexible strand 70 may be also formed of suture tape or a suture chain. The suture tapes may have the same, uniform width or may have different widths, and may comprise the same or different materials.

While the present embodiments are described herein with reference to illustrative figures for particular applications, it should be understood that the embodiments are not limited thereto. Those having ordinary skill in the art and access to the teachings provided herein will recognize additional modifications, applications, embodiments and substitution of equivalents falling within the scope of the presented embodiments. Accordingly, the embodiments are not to be considered as limited by the foregoing description.

What is claimed is:

1. A delivery device for a flexible strand, comprising: a handle; an inner member fixedly attached to the handle, the inner member having a proximal end and a distal end; a grasping mechanism provided at the distal end of the inner member; a retractable outer sheath slidably attached to the handle, the outer sheath being configured to be retractable with respect to the handle and to articulate from a first, non-retracted position to a second, retracted position and to expose the grasping mechanism when in the second, retracted position; and an actuating mechanism that retracts the outer sheath from the first, non-retracted position with respect to the handle to the second, retracted position with respect to the handle, to expose and open the grasping mechanism outside the outer sheath to an open, exposed position to allow capturing of a flexible strand and then to return the outer sheath from the second, retracted position to the first, non-retracted position to close the grasping mechanism to a closed, unexposed position wherein the grasping mechanism is housed inside the outer sheath and secure the flexible strand, the actuating mechanism comprising a rack and pinion assembly, and a housing for housing the rack and pinion assembly; and a locking mechanism configured to lock the delivery device at one or more different locking positions, wherein the locking mechanism comprises a slot in a pinion gear of the rack, the slot having a plurality of detents, a pin that is configured to sit in one of the plurality of detents when the pinion is locked, and a return spring that pushes the housing up and down relative to the outer sheath.

2. The delivery device of claim 1, wherein the retractable outer sheath is flexible and the inner member is rigid.

3. The delivery device of claim 1, wherein the retractable outer sheath is rigid and the inner member is flexible.

4. The delivery device of claim 1, wherein the actuator mechanism comprises a rack and pinion assembly formed of a rack and a pinion, and a pinion housing for housing the rack and pinion assembly.

5. The delivery device of claim 4, further comprising a locking mechanism that allows the pinion of the rack and pinion assembly to be able to translate up and down relative to the retractable outer sheath via slots provided in the pinion housing.

6. The delivery device of claim 4, wherein movement of the actuator mechanism in a first direction causes the retractable outer sheath to move in a second direction which is reversed to the first direction.

7. The delivery device of claim 1, wherein the outer sheath terminates in a most distal tip with distal edges that converge in a point to allow the outer sheath to penetrate tissue.

8. The delivery device of claim 1, wherein the grasping mechanism is formed of a segment having a U-shaped configuration.

9. The delivery device of claim 1, wherein the grasping mechanism is a snare formed of two segments having different configurations, wherein one of the two segments is straight and the other of the two segments has a U-shaped configuration.

10. The delivery device of claim 1, wherein the grasping mechanism is a snare configured to be in the closed position when the retractable outer sheath is in the first, non-retracted position, and in the open, exposed position when the retractable outer sheath is in the second, retracted position.

11. The delivery device of claim 1, wherein the flexible strand is a suture, a suture chain or a suture tape.

12. A suture passer, comprising: a handle; an inner flexible member attached to the handle, the inner flexible member having a proximal end and a distal end; a snare provided at the distal end of the inner flexible member; a retractable rigid outer sheath housing the inner flexible member and the snare, the outer sheath being configured to retract to allow the snare to be exposed and open; an actuator mechanism configured to retract the outer sheath to expose and open the snare to allow capturing of a flexible strand, and then to return to its original position to cover the snare and the captured flexible strand, the actuator comprising a rack and pinion assembly, and a housing for housing the rack and pinion assembly; and a locking mechanism configured to lock the suture passer at one or more different locking positions, wherein the locking mechanism comprises a slot in a pinion gear of the rack, the slot having a plurality of detents, a pin that is configured to sit in one of the plurality of detents when the pinion is locked, and a return spring that pushes the housing up and down relative to the outer sheath.

13. The suture passer of claim 12, wherein the locking mechanism locks the suture passer at three different locking positions.

14. The suture passer of claim 12, wherein the actuator mechanism is moved in a forward position relative to the handle to cause the outer sheath to move in a backward reverse position relative to the handle.

15. A method of delivering suture to an area during a surgical procedure, the method comprising the steps of: providing a suture delivery instrument as recited in claim 1; inserting the suture delivery instrument through a portal and with the outer sheath in the first, non-retracted position;

retracting the outer sheath to expose and open the suture grasping mechanism; and capturing suture with the opened suture grasping mechanism.

16. The method of claim 15, wherein the suture grasping mechanism is a suture snare.

17. The method of claim 15, wherein the outer sheath terminates in a most distal tip with distal edges that converge in a point, and wherein the method further comprises the step of penetrating tissue with the outer sheath.

18. The method of claim 15, wherein the surgical procedure is an endoscopic or open procedure.

* * * * *